(12) United States Patent
Carter

(10) Patent No.: US 7,541,468 B2
(45) Date of Patent: Jun. 2, 2009

(54) PROCESS OF PREPARING N-UREIDOALKYL-PIPERIDINES

(75) Inventor: Percy H. Carter, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 597 days.

(21) Appl. No.: 11/149,410

(22) Filed: Jun. 9, 2005

(65) Prior Publication Data
US 2005/0277666 A1    Dec. 15, 2005

Related U.S. Application Data

(60) Provisional application No. 60/578,784, filed on Jun. 10, 2004.

(51) Int. Cl.
C07D 211/26    (2006.01)
(52) U.S. Cl. .................. 546/231; 546/207; 548/452
(58) Field of Classification Search .............. 546/207, 546/231; 548/452
See application file for complete search history.

(56) References Cited

U.S. PATENT DOCUMENTS

| | | | | |
|---|---|---|---|---|
| 6,331,541 B1 * | 12/2001 | Ko et al. | .................. | 514/237.2 |
| 7,019,007 B2 * | 3/2006 | Du Bois et al. | ........ | 514/252.13 |
| 7,183,270 B2 * | 2/2007 | Cherney et al. | ........ | 514/210.18 |
| 7,351,720 B2 * | 4/2008 | Ko et al. | ...................... | 514/326 |
| 7,378,409 B2 * | 5/2008 | Carter et al. | ........... | 514/210.18 |
| 2004/0186140 A1 | 9/2004 | Cherney et al. | | |
| 2004/0259914 A1 | 12/2004 | Ko et al. | | |

OTHER PUBLICATIONS

CA141:225304, Cherney et al. "Preparation of cyclohexyl . . . " (2004).*
Carter et al. Preparation of substituted . . . CA 142:316496 (2005).*
Abell, A.D. et al., "Synthesis of Substituted Cyclohexenyl-Based β-Amino Acids by Ring-Closing Metathesis", Organic Letters, vol. 4, No. 21, pp. 3663-3666 (2002).
Bolm, C. et al., "Practical and Highly Enantioselective Ring Opening of Cyclic *Meso*-Anhydrides Mediated by Cinchona Alkaloids", J. Org. Chem. vol. 65, No. 21, pp. 6984-6991 (2000).
Fujita, M. et al., "Regiocontrolled Iodoaminocyclization Reaction of an Ambient Nucleophile Mediated by Basic Metallic Reagent", J. Org. Chem., vol. 62, No. 21, pp. 7330-7335 (1997).
Kobayashi, S. et al., "Creation of Novel Chiral Synthons with Enzymes and Applications to Natural Product Synthesis. 15. Efficient Introduction of Chiral Centers Into Cyclohexane Ring", Tetrahedron Letters, vol. 25, No. 24, pp. 2557-2560 (1984).
Tormo, J. et al., "Tributylstannane (Bu₃SnH)-Catalyzed Barton-McCombie Deoxygenation of Alcohols: 3-deoxy-1,2:5,6-bis-O-(1-methylethylidene)-α-D-ribo-hexofuranose (α-D-ribo-hexofuranose, 3-deoxy-1,2:5,6-bis-O-(1-methylethylidene)-)", Org. Syn., vol. 78, pp. 239-248 (2002).
Wipf, P. et al., "Diels-Alder approaches to ring-functionalized cyclic β-amino acids", Tetrahedron Letters, vol. 41, pp. 8747-8751 (2000).

U.S. Appl. No. 60/478,022, filed Dec. 12, 2003.

* cited by examiner

*Primary Examiner*—Celia Chang
(74) *Attorney, Agent, or Firm*—Mary K. VanAtten

(57) ABSTRACT

The present application describes a process of preparing a compound of formula (IV),

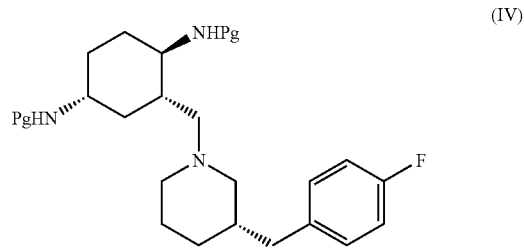

(IV)

or salt or stereoisomer thereof: wherein
Pg, at each occurrence, is independently selected from an amine protecting group;
comprising the steps of reacting a compound of Formula

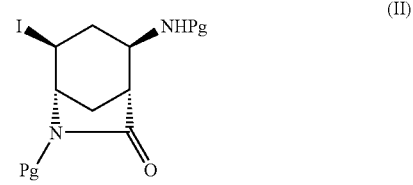

(II)

with a reducing agent to give a compound of Formula III:

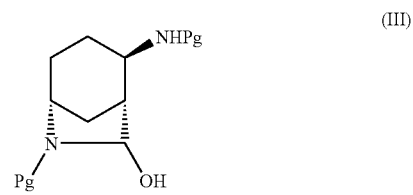

(III)

reacting the compound of formula (III) with an amine of formula (IIa) using reductive amination to give the compound of formula (III)

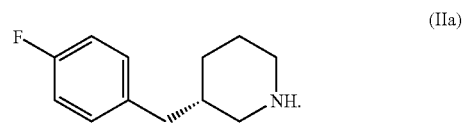

(IIa)

7 Claims, No Drawings

PROCESS OF PREPARING N-UREIDOALKYL-PIPERIDINES

This application claims a benefit of priority from U.S. Provisional Application No. 60/578,784, filed Jun. 10, 2004, the entire disclosure of which is herein incorporated by reference.

Compounds disclosed in co-pending patent application Ser. No. 10/865,417, filed Jun. 10, 2004, are modulators of chemokine receptor activity. These compounds are represented by the compound of formula (I). What is needed is process for preparing those compounds and intermediates thereof.

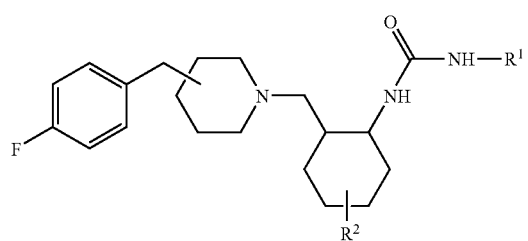
(I)

In one embodiment, the present disclosure is directed to a process of preparing a compound of formula (IV),

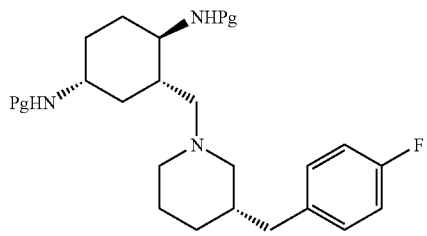
(IV)

or salt or stereoisomer thereof: wherein
  Pg, at each occurrence, is independently selected from an amine protecting group;
  comprising the steps of reacting a compound of Formula II,

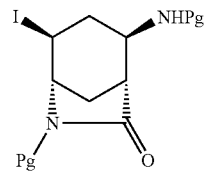
(II)

with a deiodinator and reducing agent to give a compound of Formula III;

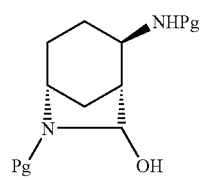
(III)

reacting the compound of formula (III) with an amine of formula (IIa) using reductive amination to give the compound of formula (II)

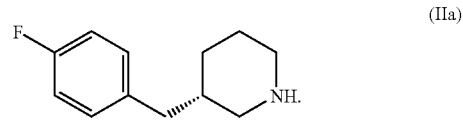
(IIa)

In another embodiment, the disclosure is directed to a process of forming compounds of formula (I) wherein the reducing agent includes a deiodinator and a reducing agent.

In another embodiment, the disclosure is directed to a process of forming compounds of formula (I) wherein the deiodinator is selected from tris-(trimethylsilyl)silane, zinc metal, tributyltin hydride AIBN (2,2'-Azobisisobutyronitrile), and the reducing agent is selected from DIBAL-H.

In another embodiment, the disclosure is directed to a process of forming compounds of formula (I) wherein the reductive amination is performed in the presence of Na(OAc)$_3$BH.

In another embodiment, the disclosure is directed to a process of preparing a compound of formula (IV),

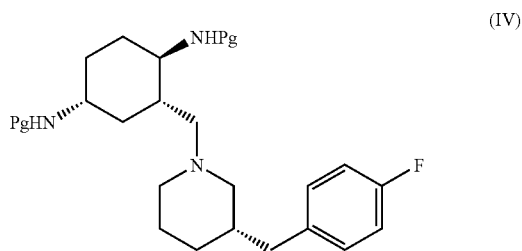
(IV)

or salt or stereoisomer thereof: wherein
  Pg, at each occurrence, is independently selected from an amine protecting group;
  comprising the steps of reacting a compound of Formula III

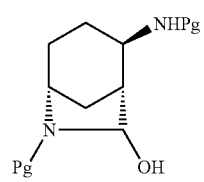
(III)

with an amine of formula (IIa) using reductive amination to give the compound of formula (II)

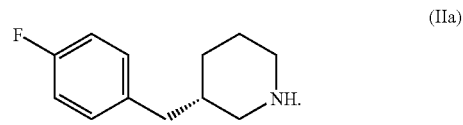
(IIa)

In another embodiment, the disclosure is directed to a process of forming compounds of formula (I) wherein the reductive amination is performed in the presence of Na(OAc)$_3$BH, NaCNBH$_3$, or Ti(iPrO)$_3$ with NaBH$_4$.

In another embodiment, the present disclosure is directed to a compound of Formula (III)

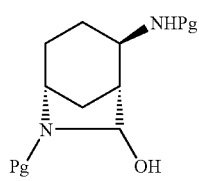

(III)

or salt or stereroisomer thereof, wherein
Pg, at each occurrence, is independently selected from an amine protecting group.

In another embodiment, the present disclosure is directed to a compound of Formula (IV)

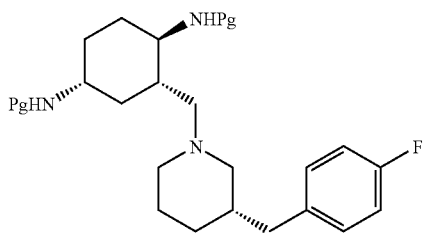

(IV)

or salt or stereroisomer thereof, wherein
Pg, at each occurrence, is independently selected from an amine protecting group.

In another embodiment, the present disclosure is directed to a compound of Formula (III) or (IV) wherein
Pg, at each occurrence, is independently selected from CBz and BOC.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^5$) occurs more than one time in any constituent or formula for a compound, its definition at each occurrence is independent of its definition at every other occurrence. Thus, for example, if a group is shown to be substituted with 0-2 $R^5$, then said group may optionally be substituted with up to two $R^5$ groups and $R^5$ at each occurrence is selected independently from the definition of $R^5$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. The "amine protecting group" should be compatible with other reaction conditions. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: 1) acyl types such as formyl, trifluoroacetyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boa), ethoxycarbonyl, diisopropylmethoxycarbonyl, and allyloxycarbonyl; and 4) cyclic alkyl carbamate types such as cyclopentyloxycarbonyl and adamantyloxycarbonyl.

Amine protecting groups may include, but are not limited to the following: 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl) methyloxycarbonyl; or 2-furanylmethyloxycarbonyl.

A suitable selective "deiodinator", also referred to as a reducing agent, is a reagent or combination of reagents which will selectively reduce (reducing agent) the W or I group in the compound of Formula (II) to a hydrogen without altering the character of the other substituents. Suitable selective deiodinators include, but are not limited to, tris-(trimethylsilyl)silane, zinc metal, tributyltin hydride and catalytic versions, see Gregory Fu, Org. Syn. (2002), 78, 239-248 which is hereby incorporated by reference, and AIBN (2,2'-Azobisisobutyronitrile).

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are envisioned for this invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

Compounds of copending patent application (PH7371 NP, filed Jun. 10, 2004) could be synthesized using the procedures summarized in Schemes 1-5 below. The commercially available 1,4-cyclohexanedione mono-ethylene ketal is treated with NaH and diethylcarbonate to give the keto ester 1 as shown in Scheme 1. The keto ester 1 is then condensed with the commercially available chiral amine R-(+)-α-methylbenzyl amine to give the ene-amine 2. Reduction of the ene-amine 2 with sodium triacetoxyborohydride (STAB) or hydrogenation at 250 psi over $PtO_2$ gives the cis β-amino ester 3. The cis β-amino ester is isomerized to the trans isomer 4 with sodium tert-butoxide in THF. The ester is reduced with lithium aluminum hydride (LAH) to give the alcohol 5. The benzyl amine of 5 is hydrogenated over $Pd(OH)_2$ on carbon at 50 psi of hydrogen to give the amino alcohol 6. The amino group of 6 is protected as the benzyl carbamate by treatment with benzyl chloroformate to give the CBZ protected amine 7 as shown in Scheme 1. Alternatively, other compatible amine protecting groups may be used in place of CBZ to protect the amine. Swern oxidation of 7 provides the aldehyde 8 as shown in Scheme 2. Reductive amination of the aldehyde with 3S-(4-F-benzyl)piperidine gives the corresponding piperidine 9. The cyclic ketal of 9 is removed by treatment with aqueous HCl to provide the ketone 10 as summarized in Scheme 2. The ketone 10 can be reductively aminated to give a mixture of R and S isomers. The ratio of isomers that is obtained depends on the method used as summarized in Scheme 3 using methylamine as the example. Using STAB as the reducing agents gives mainly the S isomer when the reaction is run in dilute solutions and approximately a 1:1 ratio of R/S amine isomers under more concentrated reaction conditions. Using $NaCNBH_3$ as the reducing agent gives a 1:1 ratio of isomers, whereas, the use of titanium isopropoxide and $NaBH_4$ generally gives the R isomer, 11, as the major product as shown in Scheme 3. The amine 11 is reacted with acetic anhydride to give the amide 12. The primary amine protecting group of 12 is removed using catalytic hydrogenation (10% Pd/C) at 55 psi in methanol to give the free amine 13 as shown in Scheme 4. The amine is treated with the phenyl carbamate in THF at room temperature to give the desired urea 14 in good yields. The ketone intermediate 10 can undergo reductive amination with a wide variety of secondary amines ($HNR^aR^b$, Scheme 5) to give the tertiary amines 15. Some of the secondary amine that were used includes dimethylamine, piperidine, morpholine, and piperazinone. The tertiary amines 15, are then hydrogenated to remove the CBZ protecting group and the resulting free amine can be treated with carbamates or isocyanates to give a variety of ureas 16 as shown in Scheme 5. Alternatively, the ketone intermediate 10 can be reductively aminated with ammonia or primary amines ($NH_2R^a$, Scheme 5) to give the corresponding primary or secondary amine 17. This primary amine can then be treated with $Boc_2O$ or methanesulfonyl chlorides to give 18 ($R^c$=Boc or Mesyl) as shown in Scheme 5. The amines 18, are then hydrogenated to remove the CBZ protecting group and the resulting free amine can be treated with carbamates or isocyanates to give a variety of ureas 19. When $R^c$ of 19 is a Boc group, this is removed by treatment with trifluoroacetic acid to give the free amine ($R^c$=H).

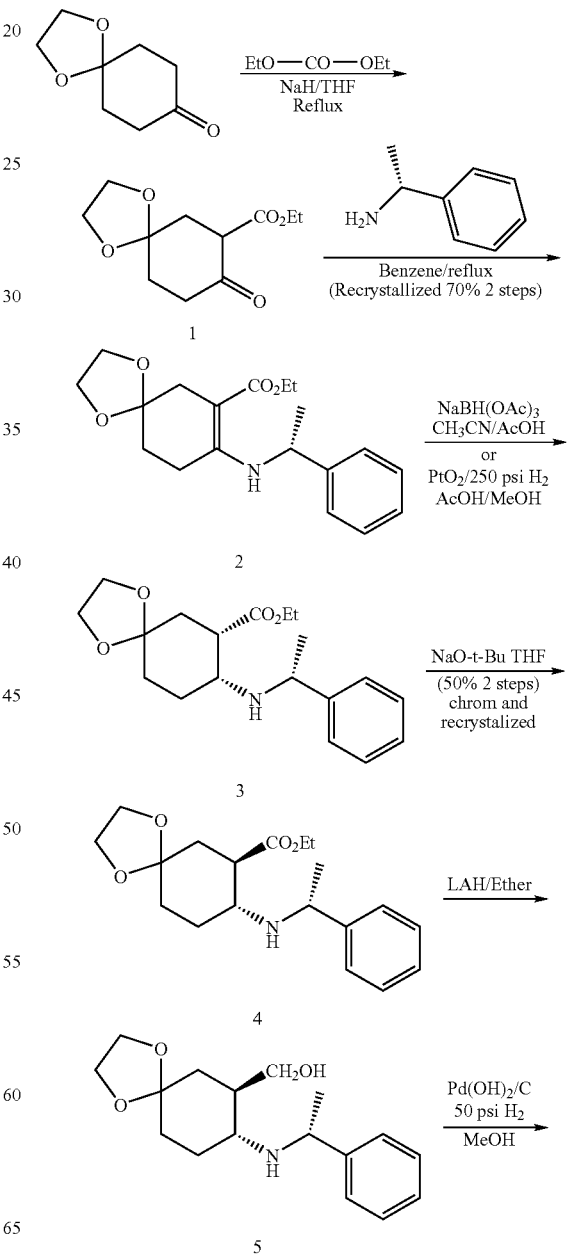

Scheme 1.

-continued
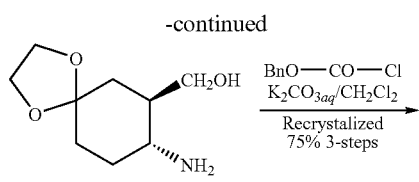
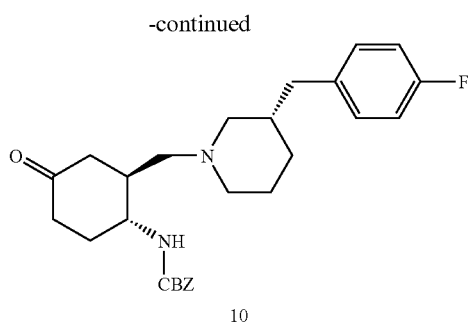
Scheme 2.
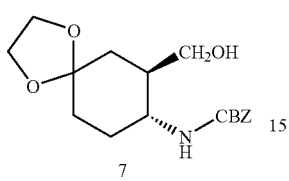
Scheme 3
Method 1:
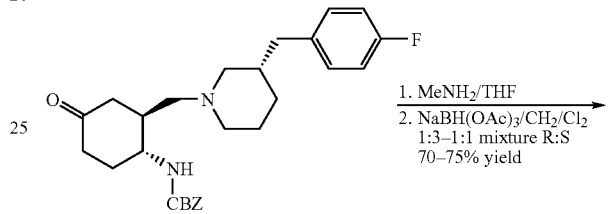
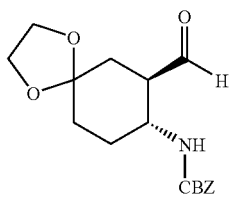
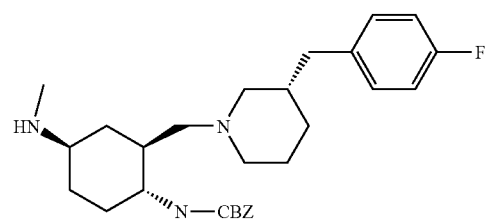
Method 2:
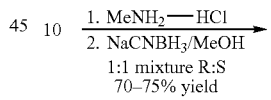
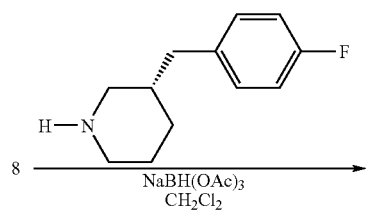
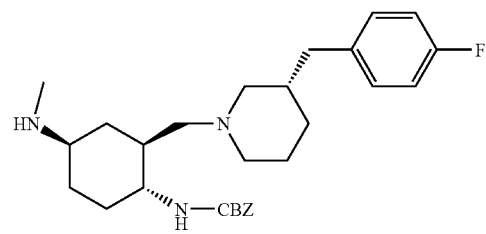
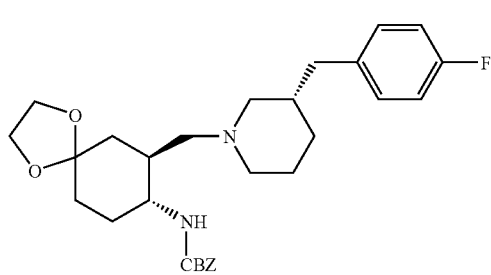
Method 3:
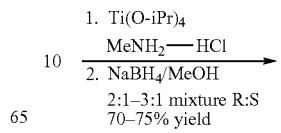
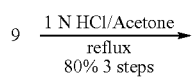

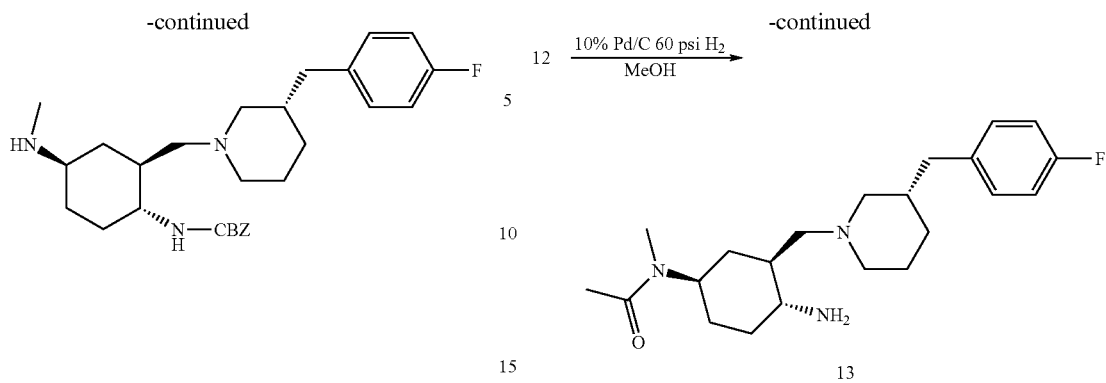
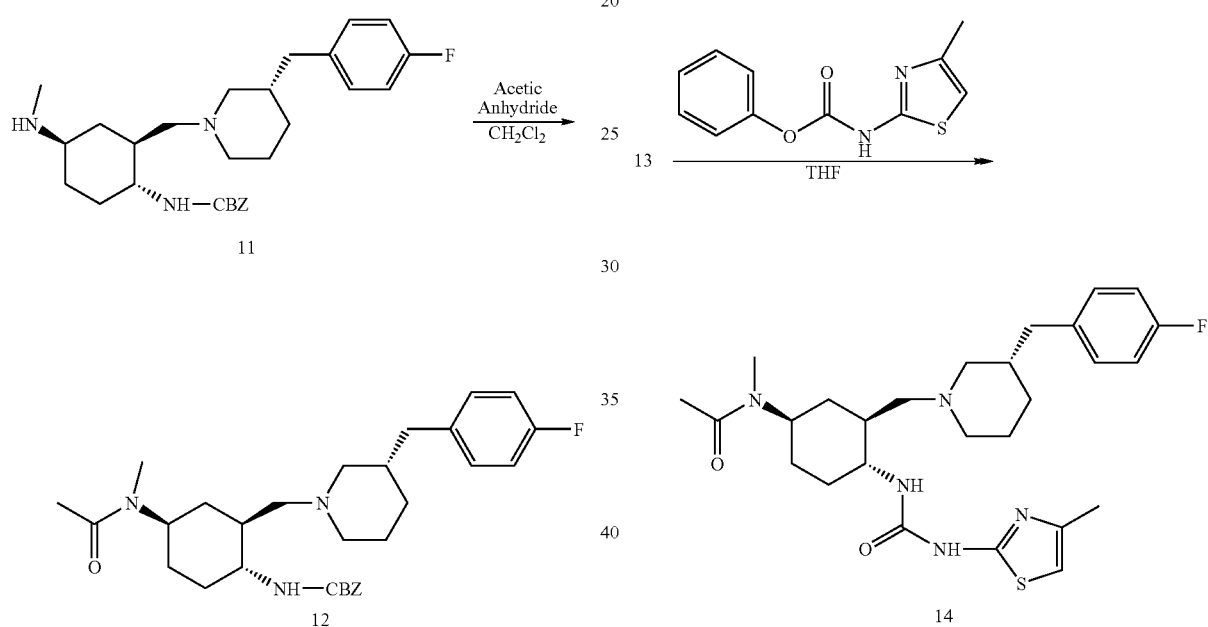
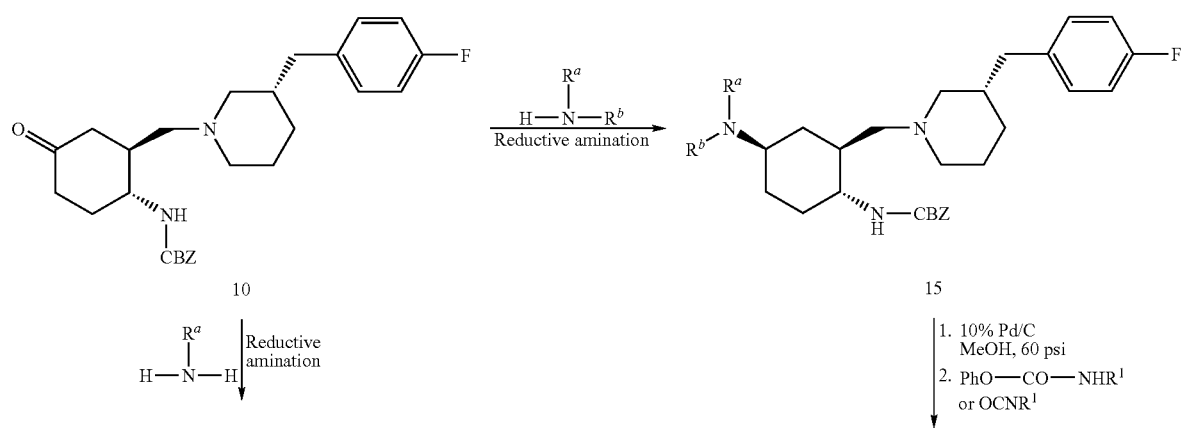

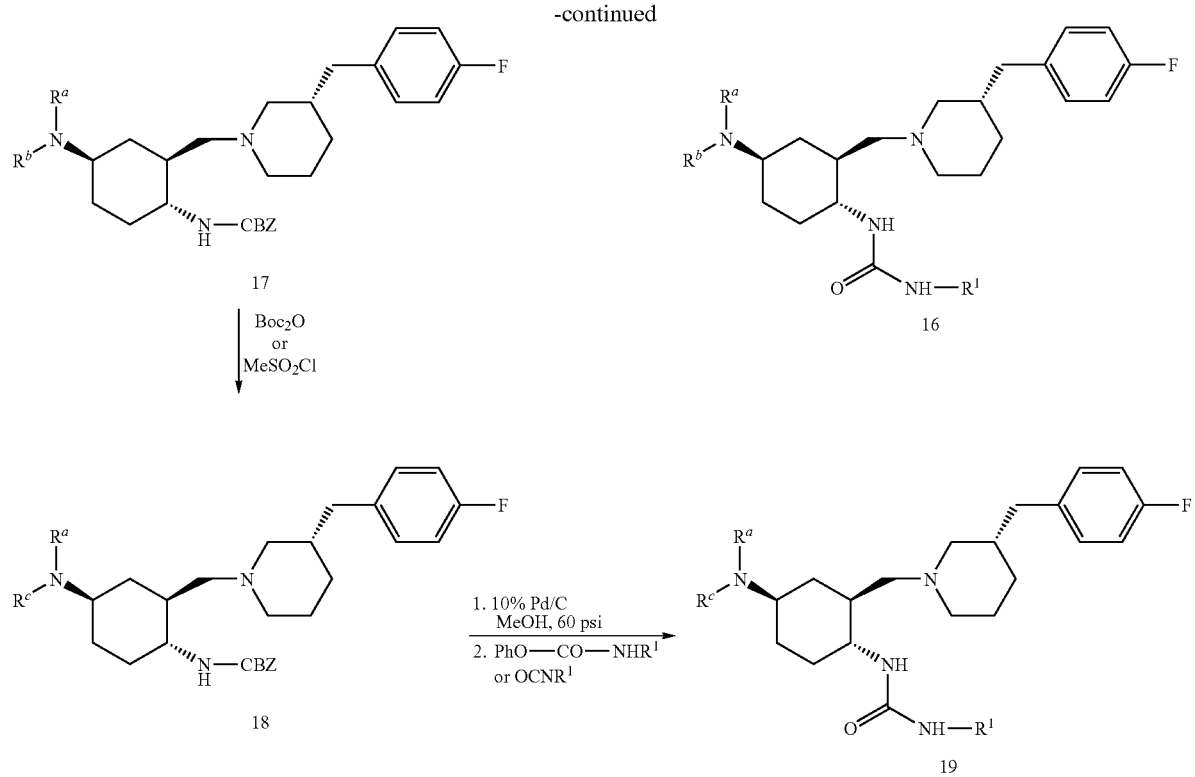

An alternative synthesis of select compounds of co-pending patent application Ser. No. 10/865,417, is shown in Scheme 8. The known protected β-aminoester 36 (Kobayashi, et al., *Tetrahedron Lett.* 1984, 25, 2557; Abell and Gardiner, *Org. Lett.* 2002, 4, 3663; Wipf and Wang, *Tetrahedron Lett.* 2000, 41, 8747) is readily hydrolyzed and then coupled with ammonia to provide amide 37, which may be further transformed to acyl carbamate 38. Cyclization of the lithio anion of 38 with iodine provides 39 (for a related reaction, see: Taguchi, et al., *J. Org. Chem.* 1997, 62, 7330). Compound 39 may be deiodinated and reduced to provide 40, which may be functionalized through reductive amination with a variety of amines. In the instance of the present invention, coupling with 3-(para-fluorobenzyl)piperidine provides compound 41. As described in the schemes above, compound 41 is readily functionalized to provide compounds, generalized in structure 42.

Scheme 8

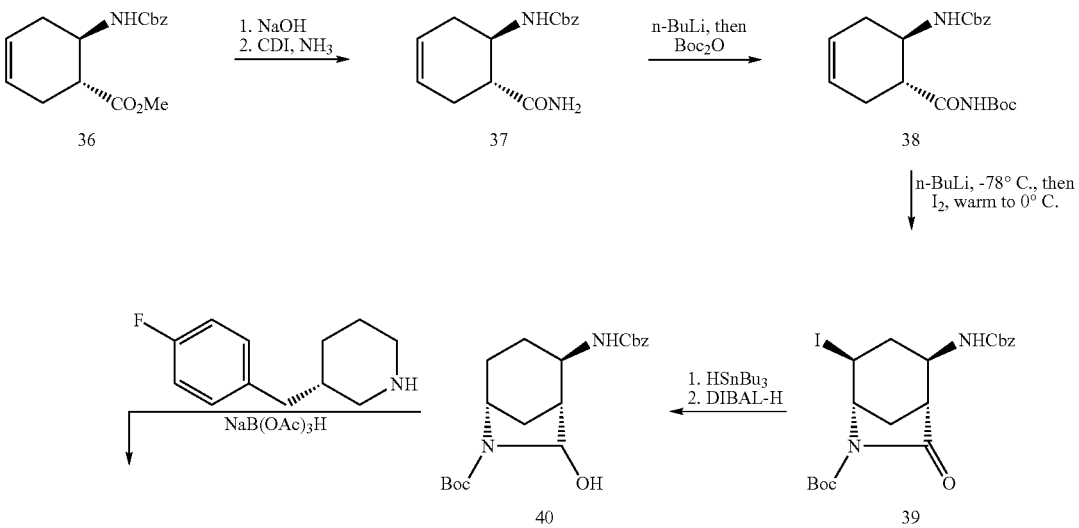

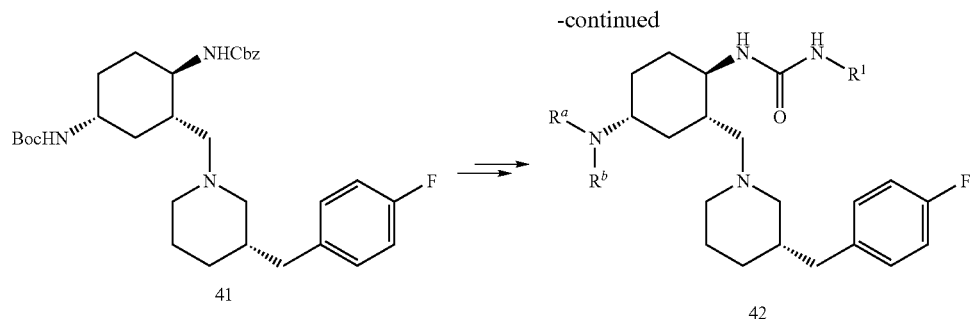

The process for forming the diastereomer of compound 39 is described in copending patent application Ser. No. 10/776,828, filed Feb. 11, 2004, the description of the process is hereby incorporated by reference. The compound 39 can be deiodinated as described in that patent application. The lactam carbonyl can be reduced using a variety of reducing agents known to one skilled in the art. Examples of reducing agents are DIBAL-H (diisobutylaluminum hydride), LiEt$_3$BH (Superhydride) and LAH (lithium aluminum hydride). Other reducing agents may also be used in this reactions The reactions are typically run in ether solvents such as diethyl ether or THF or methylene chloride or other non-reactive solvents. The reactions are typically run at temperatures of about −78° C. to about 0° C.

The reductive amination of compound 40 to 41 may occur by a variety of methods known to one skilled in the art. The reductive amination is typically run using Na(OAc)$_3$BH, NaCNBH$_3$, or Ti(iPrO)$_3$ with NaBH$_4$. Depending on the specific reaqent, the reaction may be run in halogenated solvents such as methylene chloride or dichloroethane, or alcoholic solvents such as methanol or ethanol.

More generally, the compounds may be prepared using the procedure shown in Scheme 9.

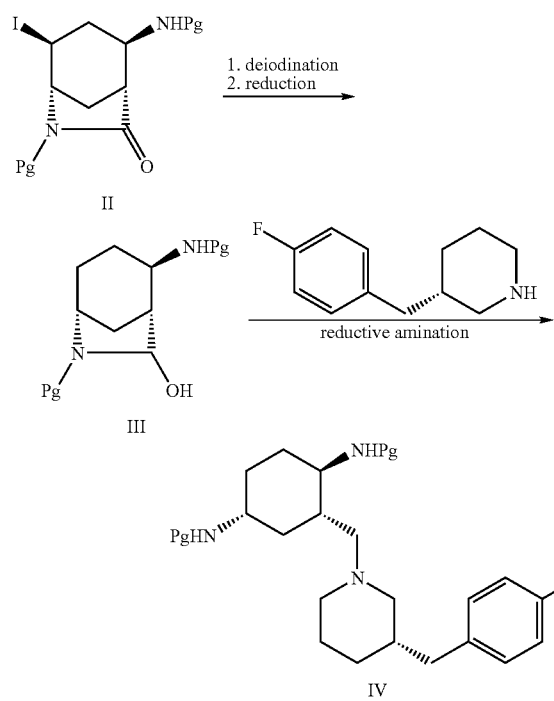

wherein Pg are amine protecting groups which may be selectively removed from the compound of formula (IV) so that the amine may be further selectively reacted to form the compounds of formula (I).

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:

1. A process of preparing a compound of formula (IV),

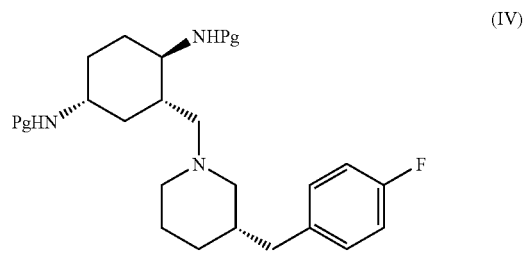

or salt or stereoisomer thereof: wherein
Pg, at each occurrence, is independently selected from an amine protecting group;
comprising the steps of reacting a compound of Formula II,

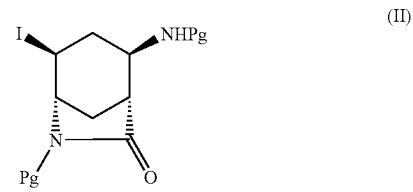

with a reducing agent to give a compound of Formula III;

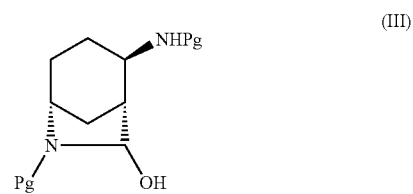

reacting the compound of formula (III) with an amine of formula (IIa) using reductive amination to give the compound of formula (IV)

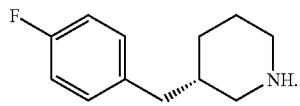
(IIa)

2. The process of claim 1, wherein the reducing agent includes a deiodinator and a reducing agent.

3. The process of claim 2, wherein the deiodinator is selected from tris-(trimethylsilyl)silane, zinc metal, tributyltin hydride AIBN (2,2'-Azobisisobutyronitrile), and the reducing agent is selected from DIBAL-H.

4. The process of claim 3, wherein the reductive amination is performed in the presence of Na(OAc)$_3$BH.

5. A process of preparing a compound of formula (IV),

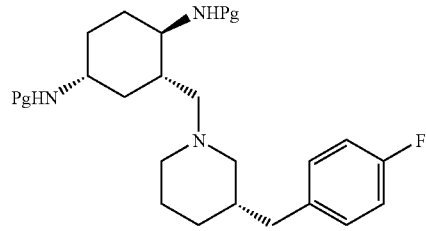
(IV)

or salt or stereoisomer thereof: wherein
Pg, at each occurrence, is independently selected from an amine protecting group;

comprising the steps of reacting a compound of Formula III

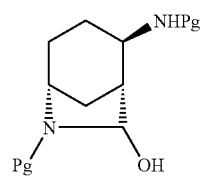
(III)

with an amine of formula (IIa) using reductive amination to give the compound of formula (IV)

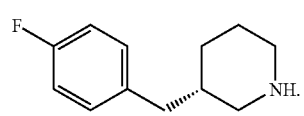
(IIa)

6. The process of claim 5, wherein the reductive amination is performed in the presence of Na(OAc)$_3$BH, NaCNBH$_3$, or Ti(iPrO)$_3$ with NaBH$_4$.

7. A compound of Formula (III)

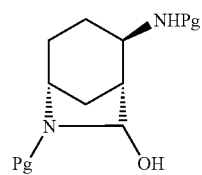
(III)

or salt or stereroisomer thereof, wherein
Pg, at each occurrence, is independently selected from an amine protecting group.

* * * * *